United States Patent
Sha Pu et al.

(10) Patent No.: US 9,277,876 B2
(45) Date of Patent: Mar. 8, 2016

(54) METHOD AND COMPUTER PROGRAM PRODUCT FOR MEASURING A METABOLIC RATE OF A USER

(71) Applicant: SPORT-SUPPORTED CULTURES INTERNATIONAL LTD., Puli, Nantou (TW)

(72) Inventors: Lu Bi Sha Pu, Ren'ai (TW); Chia-Chih Lin, Shoufong (TW); Wen-Kai Tai, Shoufong (TW); Yi-Ting Pan, Yanpu (TW); Jung-Charng Lin, Taipei (TW)

(73) Assignee: SPORT-SUPPORTED CULTURES INTERNATIONAL LTD., Puli (TW)

( * ) Notice: Subject to any disclaimer, the term of this patent is extended or adjusted under 35 U.S.C. 154(b) by 418 days.

(21) Appl. No.: 14/025,217

(22) Filed: Sep. 12, 2013

(65) Prior Publication Data
US 2014/0296652 A1     Oct. 2, 2014

(30) Foreign Application Priority Data
Apr. 1, 2013    (TW) .............................. 102111683 A

(51) Int. Cl.
*A61B 5/083*     (2006.01)
*A61B 5/145*     (2006.01)
*A61B 5/00*     (2006.01)

(52) U.S. Cl.
CPC ........... *A61B 5/0833* (2013.01); *A61B 5/14532* (2013.01); *A61B 5/6898* (2013.01)

(58) Field of Classification Search
CPC . A61B 5/0833; A61B 5/6898; A61B 5/14532
See application file for complete search history.

(56) References Cited

U.S. PATENT DOCUMENTS

2003/0208110 A1* 11/2003 Mault .................. A61B 5/0002
                                                            600/300
2004/0254501 A1* 12/2004 Mault .................... A61B 5/083
                                                            600/587

* cited by examiner

*Primary Examiner* — Gary Jackson
*Assistant Examiner* — Boniface N Nganga
(74) *Attorney, Agent, or Firm* — Nixon & Vanderhye P.C.

(57) ABSTRACT

In a method for measuring a metabolic rate of a user, an electronic device is configured to: output a first instruction to instruct the user to pronounce a first specified sound at rest; record a first vocal signal associated with the first specified sound pronounced by the user; output a second instruction to instruct the user to pronounce a second specified sound at exercise; record a second vocal signal associated with the second specified sound pronounced by the user; and evaluate the metabolic rate of the user according to the first vocal signal, the second vocal signal, and a maximum oxygen uptake of the user that is pre-obtained by the electronic device.

10 Claims, 4 Drawing Sheets

US 9,277,876 B2

METHOD AND COMPUTER PROGRAM PRODUCT FOR MEASURING A METABOLIC RATE OF A USER

CROSS-REFERENCE TO RELATED APPLICATION

This application claims priority of Taiwanese Application No. 102111683, filed on Apr. 1, 2013.

BACKGROUND OF THE INVENTION

1. Field of the Invention

The invention relates to a method and a computer program for measuring a metabolic rate of a user.

2. Description of the Related Art

As physical fitness becomes a widely sought-after goal, various fitness programs for achieving it have been designed. Typically, such programs involve adopting a proper diet and undertaking a workout routine. However, in order to tailor-make a program suitable for a particular individual, it is important to be aware of some physical characteristics of the individual, such as a metabolic rate thereof (i.e., the rate at which he/she expands energy provided by carbohydrate and/or fat).

A respiratory exchange rate (RER), standing for a ratio of a volume of carbon dioxide produced ($\dot{V}CO_2$) and a volume of oxygen consumed ($\dot{V}O_2$) of a user, is an important measurement in determination of the metabolic rate of the user at a given state, for example, at exercise.

Conventionally, in order to obtain the RER of a user at a given state (such as at exercise), a testing equipment may be used. The testing equipment includes a mask that covers the mouth and the nose of the user for collecting gas exhaled by the user at exercise, a ventilation tube that is fluidly connected to the mask, and a gas analyzing unit that receives the gas exhaled by the user through the ventilation tube, and for analyzing the collected gas to obtain a concentration of oxygen ($O_2\%$) of the collected gas, a concentration of carbon dioxide ($CO_2\%$) of the collected gas, and a minute ventilation ($\dot{V}_E$), which represents the total volume of air entering the lungs per minute. A processor of the testing equipment is then able to calculate the RER of the user based upon the above data, and subsequently obtain the metabolic rate of the user.

However, in order to calculate the RER at exercise, the user is required to exercise with the mask covering his/her mouth and nose, and such a task may be an ordeal for some. Additionally, the testing equipment is usually expensive and relatively large in size, thus having little or no portability.

SUMMARY OF THE INVENTION

Therefore, the object of the present invention is to provide a method that is for measuring a metabolic rate of a user, and that alleviates at least some of the drawbacks mentioned above.

According to this invention, there is provided a method for measuring a metabolic rate of a user. The method is implemented using an electronic device. The electronic device includes an instructing module, a voice recording module, and a processor. The method comprises the following steps of:

outputting, by the instructing module, a first instruction to instruct the user to pronounce a first specified sound at rest;

recording, by the voice recording module, a first vocal signal associated with the first specified sound pronounced by the user;

outputting, by the instructing module, a second instruction to instruct the user to pronounce a second specified sound at exercise;

recording, by the voice recording module, a second vocal signal associated with the second specified sound pronounced by the user; and evaluating, by the processor, the metabolic rate of the user according to the first vocal signal and the second vocal signal.

Another object of the present invention is to provide a computer program product for implementation of the above-mentioned method.

The computer program product comprises a non-transitory machine-readable storage medium having machine-executable program code instructions which are stored therein and which, when executed by a machine, configure the machine to execute consecutive steps of the method of this invention.

BRIEF DESCRIPTION OF THE DRAWINGS

Other features and advantages of the present invention will become apparent in the following detailed description of the preferred embodiment with reference to the accompanying drawings, of which.

DETAILED DESCRIPTION OF THE PREFERRED EMBODIMENT

Figure 1:
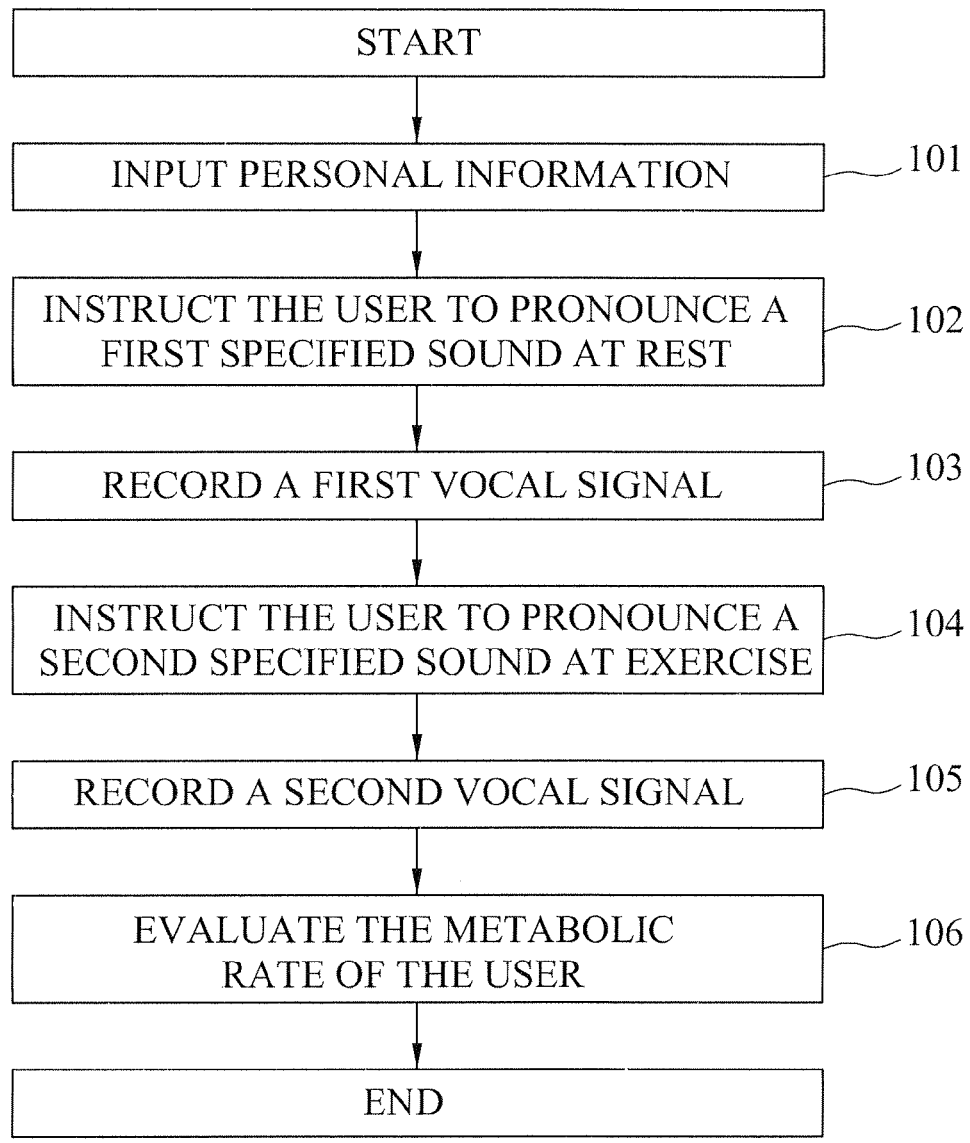
FIG. 1 is a flow chart of a preferred embodiment of a method for measuring a metabolic rate of a user, according to the invention.

Before the present invention is described in greater detail, it should be noted that like elements are denoted by the same reference numerals throughout the disclosure.

Figure 2:
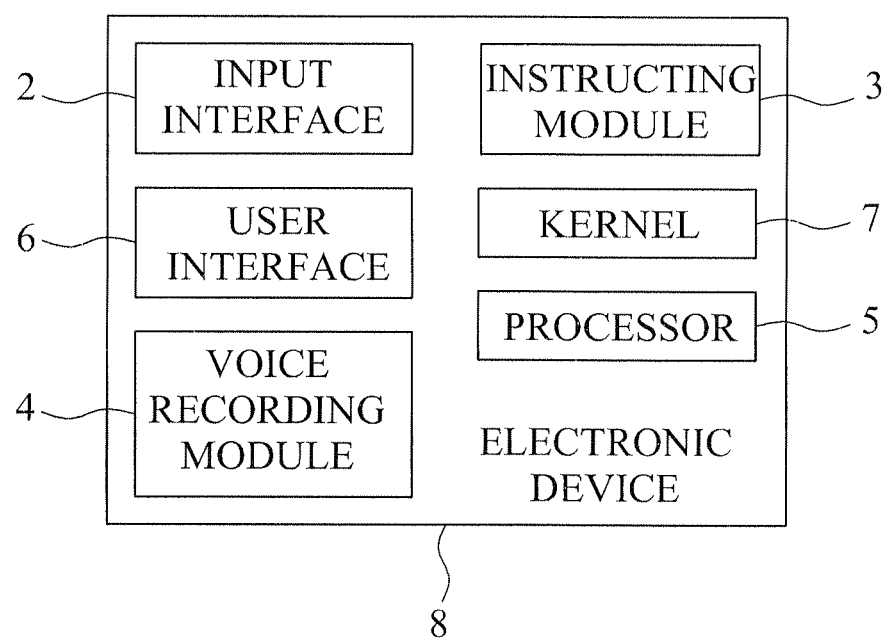
FIG. 2 is a schematic block diagram of an example of an electronic device for implementing the method.

As shown in FIGS. 1 and 2, the preferred embodiment of a method according to the present invention may be embodied as an application program, which may be implemented using an electronic device 8, as shown in FIG. 2.

The electronic device 8 may be a portable device such as a smart phone, a laptop computer, a tablet computer, a personal digital assistant (PDA), etc. In this embodiment, the electronic device 8 is a smart phone, and includes an input interface 2, an instructing module 3, a voice recording module 9, a processor 5, and a kernel 7. In other embodiments, any other suitable electronic devices having the capability to execute the application program may be used.

The input interface 2 is embodied as a touch screen of the electronic device 8. The instructing module 3 is embodied as a speaker built in the electronic device 8, but may be implemented using an external portable speaker in other embodiments. The voice recording module 4 is embodied as a microphone built in the electronic device 8, but may be implemented using an external microphone in other embodiments. The kernel 7 is a computer program built in the electronic device 8 for managing interactions between the application program and the hardware components of the electronic device 8.

The application program, when executed by the electronic device 8, generates a user interface (UI) that provides a user with information during implementation of the method. The method will now be described in detail in the following paragraphs.

In step 101 of the method, the UI 6 of the electronic device 8 instructs the user to input personal information thereof. The personal information includes a gender of the user, an age of the user, a weight of the user, and a maximum oxygen uptake of the user.

The maximum oxygen uptake, also known as a maximum volume of oxygen consumed ($VO_2$ max), is defined as the "maximum capacity of an individual's body to transport and to use oxygen during incremental exercise at sea level", and is expressed in milliliters (or liters) of oxygen per kilogram of bodyweight per minute (ie, mL/(kg·min) or L/(kg·min)). $VO_2$ max of a particular user may be measured by taking a graded exercise test (GXT) on a cycle ergometer or a treadmill. During the GXT, the intensity of the exercise is gradually increased, until the maximum consumption of oxygen is reached. In this embodiment, it is assumed that the $VO_2$ max is already known to the user.

In step 102, the instructing module 3 outputs a first instruction to instruct the user to pronounce a first specified sound at rest. Specifically, the instructing module 3 outputs the first instruction with a plurality of first sections by a particular rhythm to instruct the user to pronounce the first specified sound in one breath.

In one example, the first instruction includes a string of short beep sounds outputted with a tempo of 120 beats per minute (BPM). In response, the user says a string of words, which correspond to the tempo of the short beep sounds and which serve as the first specified sound, by a normal sound volume in one breath. For example, the string of words may be "one, two, three, four" or its variations. The user may stop saying when he/she feels uncomfortable or is unable to continue.

In step 103, the first specified sound provided by the user is recorded by the voice recording module 4 as a first vocal signal, which includes a plurality of first sound segments corresponding respectively to the first sections.

Subsequently, in step 104, the instructing module 3 outputs a second instruction to instruct the user to pronounce a second specified sound at exercise. Similar to step 102, the instructing module 3 outputs the second instruction with a plurality of second sections by a particular rhythm to instruct the user to pronounce the second specified sound in one breath. In some embodiments, the second instruction is identical to the first instruction. In step 105, the second specified sound pronounced by the user is recorded by the voice recording module 4 as a second vocal signal, which includes a plurality of second sound segments corresponding respectively to the second sections.

Then, in step 106, the processor 5 evaluates the metabolic rate of the user according to the first and second vocal signals, and the maximum oxygen uptake of the user. The evaluation is done as follows, with reference to FIG. 3.

First, the processor 5 cooperates with the kernel 7 to measure respective durations of the first and second vocal signals (blocks 602 and 604), and to calculate a proportional relation between the durations of the first and second vocal signals (block 610). Specifically, the proportional relation is defined as the duration of the second vocal signal divided by the duration of the first vocal signal.

Afterward, the processor 5 calculates an oxygen uptake rate (OUR) (block 620) and a respiratory exchange ratio (RER) (block 630) of the user at exercise, based on the proportional relation.

The OUR of the user at a given state indicates the capacity of oxygen utilized by the user, and is positively related to the intensity of exercise. With very high intensity, the OUR of the user at the moment may approach the $VO_2$ max.

In this embodiment, the OUR is calculated using an OUR equation, and is expressed as a proportion of the $VO_2$ max. The OUR equation may be obtained by linear regression, and includes a set of parameters that are be adjusted according to various personal information, such as gender.

For example, the OUR equation for a male user is (−99.287*the proportional relation+103.1)/100, while for a female user, the OUR equation is adjusted to (−97.356*the proportional relation+106.62)/100. Thus, if the electronic device 8 obtains a 15-second long first vocal signal and a 9-second long second vocal signal from a male user, his OUR is then given, using the above OUR equation, by (−99.287*(9/15)+103.1)/100)=0.4353. If the electronic device 8 obtains a 12-second long first vocal signal and a 7.2-second long second vocal signal from a female user, her OUR is then given, using the above OUR equation, by (−97.356*(7.2/12)+106.62)/100)=0.4821.

The RER of the user is a ratio of a volume of carbon dioxide produced ($VCO_2$) to a volume of oxygen consumed ($VO_2$). Normally the RER of a person ranges from 0.7 to 1.2. In this embodiment, the RER is calculated using an RER equation, which may be similarly obtained by linear regression, and includes a set of parameters that may be adjusted based on various personal information, such as gender.

For example, the RER equation for a male user is (−0.3542*the proportional relation+1.0632), while for a female user, the RER equation is adjusted to (−0.3549*the proportional relation+1.0582). Thus, if the electronic device 8 obtains a 15-second long first vocal signal and a 9.75-second long second vocal signal from a male user, his RER is then given, using the above RER equation, by (−0.3542*(9.75/15)+1.0632)=0.8330. If the electronic device 8 obtains a 12-second long first vocal signal and a 7.8 second long second vocal signal from a female user, her RER is then given, using the above RER equation, by (−0.3549(7.8/12)+1.0582)=0.8275.

After the OUR and RER of the user are obtained, in block 650, the metabolic rate, including a glucose metabolic rate and a fat metabolic rate, can be calculated. Specifically, the glucose metabolic rate and the fat metabolic rate may be separately calculated by associated equations obtained using linear regression, according to the personal information, and the OUR and RER of the user.

In this embodiment, the glucose metabolic rate (grams per minute) of the user is calculated by weight* (OUR*$VO_2$max) *(4.19486*RER−2.97867). It is noted that, (OUR*$VO_2$max) stands for a current oxygen uptake (block 640), i.e., the volume of oxygen the user utilizes at the moment. For example, consider a user with a weight of 50 kilograms, a $VO_2$max of 2.5 L/(kg·min), an OUR of 0.8, and an RER of 0.85. His/her glucose metabolic rate is then found to be 1.17392 grams per minute.

A similar equation can be applied to evaluate the fat metabolic rate of the user. In this embodiment, the fat metabolic rate (grams per minute) of the user is calculated by weight* (OUR*$VO_2$max)* (−1.6982*RER+1.69225). For example, the user as described in the above paragraph has a fat metabolic rate of 0.49756 grams per minute.

It is noted that, if the $VO_2$max of the user is not known before the method, the application program may require the user to perform an impromptu test. For example, in a case where the electronic device 8 is embodied as an embedded computing module of a cycle ergometer or a treadmill, the VO₂ max may be estimated using result of a Balke treadmill test (i.e., the total time the user is able to endure). Alternatively, the user may be instructed to perform a Cooper test (e.g., to perform a 12-minute run or a 1.5 mile run), and the electronic device 8 estimates the VO₂max based on the result (i.e., the distance during the 12-minute run or the time to complete the 1.5 mile run) and the personal information. The following Table 1 is an excerpt from the American College of Sports Medicine (ACSM)'s Guidelines for Exercise Testing and Prescription, and can be used to estimate the VO₂max associated with various performance data of users between the ages of 20 to 29.

TABLE 1

Ages: 20-29

| Estimated VO₂max (mL/min/kg) | Time on Balke treadmill test (Mins) | Cooper 12-minute distance (KM) | Cooper 1.5-mile run time (min:sec) |
| --- | --- | --- | --- |
| 61.2 | 32.00 | 2.02 | 8:22 |
| 56.2 | 28.31 | 1.88 | 9:10 |
| 54.0 | 27.00 | 1.81 | 9:34 |
| 52.5 | 26.00 | 1.77 | 9:52 |
| 51.1 | 25.00 | 1.73 | 10:08 |

In other embodiments, the input interface 2 and the instructing module 3, may be both embodied as a touch screen. While in the previous embodiment, each of the sections included in the first and second instructions is provided by the instructing module 3 in the form of audio, the sections may be provided in the form of an image in other embodiments.

For example, in steps 102 and 104 of the method, the instructions may include a string of images outputted with a frequency of 120 images per minute. Accordingly, the user provides the first and second specified sounds based on what he/she sees.

Figure 3:
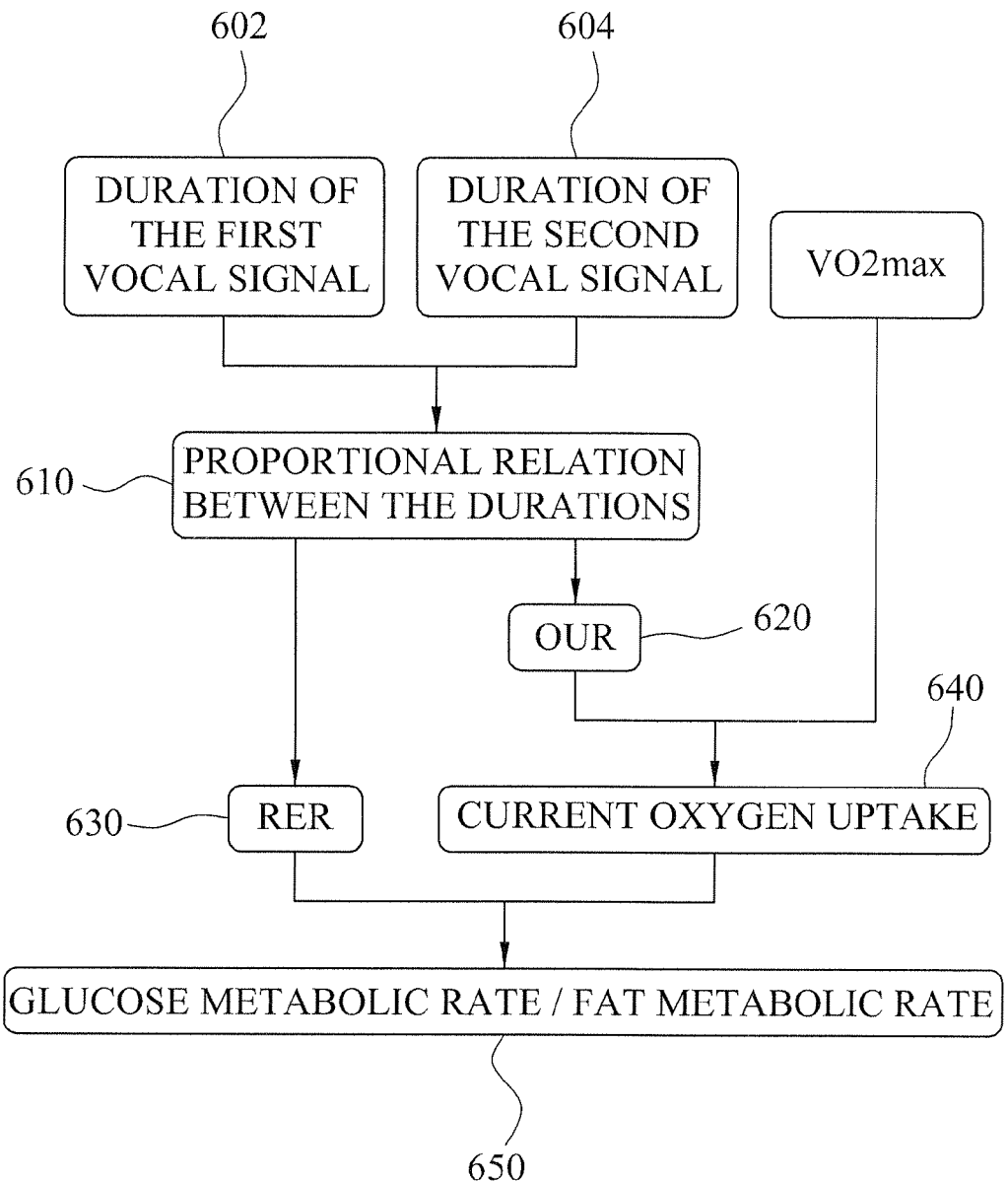
FIG. 3 illustrates a relational sequence of parameters that are sequentially calculated by the electronic device in the method for obtaining the metabolic rate of the user.
Figure 4:
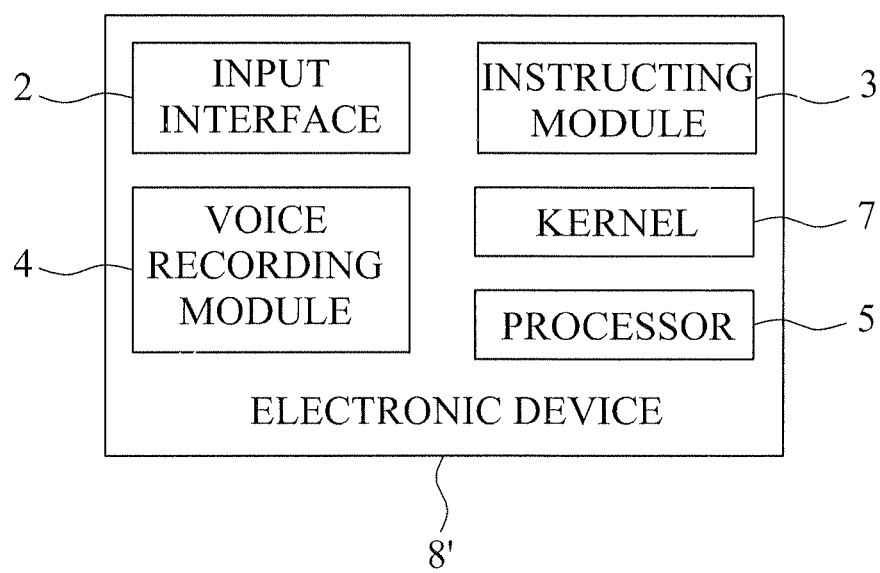
FIG. 4 is a schematic block diagram of another example of an electronic device for implementing the method.

As shown in FIGS. 1, 3 and 4, another example of an electronic device 8' used to implement the method for measuring the metabolic rate of the user has a structure similar to that of the electronic device 8 shown in FIG. 2. The main difference between the electronic device 8' of this example and the electronic device 8 resides in the following.

The electronic device 8' in this example is embodied as a media playing assembly, such as a combination of an mp3 player and a headset. The input interface 2 is embodied as a button set on the mp3 player for controlling operation of the same. The instructing module 3 and the voice recording module 4 are embodied commonly as a headset (headphones combined with a microphone). The processor 5 is embodied as a central processor unit (CPU) of the electronic device 8'. The kernel 7 may be built-in firmware of the mp3 player.

To sum up, the method and the electronic devices 8, 8' of the present invention provide a relatively convenient approach to estimate the metabolic rate of the user without employing the costly testing equipments or having the user wear a mask while working out. Additionally, since the method of the present invention can be carried out using a portable device, the present invention provides enhanced mobility.

While the present invention has been described in connection with what are considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A method for measuring a metabolic rate of a user, said method to be implemented using an electronic device that includes an instructing module, a voice recording module, and a processor, said method comprising the following steps of:

outputting, by the instructing module, a first instruction to instruct the user to pronounce a first specified sound at rest;

recording, by the voice recording module, a first vocal signal associated with the first specified sound pronounced by the user;

outputting, by the instructing module, a second instruction to instruct the user to pronounce a second specified sound at exercise;

recording, by the voice recording module, a second vocal signal associated with the second specified sound pronounced by the user; and evaluating, by the processor, the metabolic rate of the user according to the first vocal signal, the second vocal signal, and a maximum oxygen uptake of the user that is pre-obtained by the electronic device.

2. The method of claim 1, wherein the step of evaluating the metabolic rate includes the following sub-steps of:

measuring respective durations of the first and second vocal signals; and calculating the metabolic rate of the user based on a proportional relation between the durations of the first and second vocal signals.

3. The method of claim 2, wherein the step of evaluating the metabolic rate further includes the following sub-steps of:

calculating an oxygen uptake rate (OUR) and a respiratory exchange ratio (RER) of the user at exercise, based on the proportional relation between the durations of the first and second vocal signals; and calculating the metabolic rate of the user based on the OUR and the RER.

4. The method of claim 3, wherein the metabolic rate includes a glucose metabolic rate and a fat metabolic rate, and the step of evaluating the metabolic rate includes the following sub-steps of:

calculating a current oxygen uptake of the user based on the OUR and the maximum oxygen uptake of the user; and calculating the glucose metabolic rate and the fat metabolic rate based on the current oxygen uptake and the RER of the user.

5. The method of claim 3, wherein the OUR and the RER are calculated using an OUR equation and an RER equation, respectively, and the OUR equation and the RER equation are obtained by linear regression.

6. The method of claim 5, wherein, in the sub-step of calculating the OUR and the RER, the processor of the electronic device adjusts a set of parameters of each of the OUR equation and the RER equation according to personal information of the user that is pre-obtained by the electronic device.

7. The method of claim 6, wherein the personal information of the user includes at least one of a gender of the user, an age of the user, a weight of the user, and the maximum oxygen uptake of the user.

8. The method of claim 1, wherein, in each of the sub-steps of outputting the first and second instructions, the instructing module of the electronic device outputs a corresponding one of the first and second instructions with a plurality of sections by a particular rhythm to instruct the user to pronounce a corresponding one of the first and second specified sounds in one breath, and each of the first and second vocal signals includes a plurality of sound segments corresponding respectively to the sections of the corresponding one of the first and second instructions.

9. The method of claim 8, wherein the instructing module of the electronic device includes at least one of a speaker and a display screen, and each of the sections includes at least one of an audio and an image.

10. A computer program product comprising a non-transitory machine-readable storage medium having machine-executable program code instructions which are stored therein and which, when executed by a machine, configure the machine to execute consecutive steps of the method of claim 1.

* * * * *